United States Patent
Chow et al.

(10) Patent No.: US 7,458,943 B1
(45) Date of Patent: Dec. 2, 2008

(54) SPINE TILT MONITOR WITH BIOFEEDBACK

(75) Inventors: Daniel Hung Kay Chow, Hong Kong (HK); Malcolm H Pope, Stonehaven (GB)

(73) Assignee: The Hong Kong Polytechnic University, Kowloon (HK)

( * ) Notice: Subject to any disclaimer, the term of this patent is extended or adjusted under 35 U.S.C. 154(b) by 0 days.

(21) Appl. No.: 11/819,002

(22) Filed: Jun. 25, 2007

(51) Int. Cl.
*A61B 5/117* (2006.01)
*A61B 5/103* (2006.01)

(52) U.S. Cl. ..................................................... 600/595

(58) Field of Classification Search ................ 600/300, 600/587, 594, 595, 25; 33/512; 473/450; 381/23.1; 307/140; 323/287; 327/435, 478
See application file for complete search history.

(56) References Cited

U.S. PATENT DOCUMENTS

| | | | |
|---|---|---|---|
| 4,633,094 A * | 12/1986 | Knudsen ..................... 307/140 |
| 5,158,089 A | 10/1992 | Swezey et al. |
| 5,919,149 A * | 7/1999 | Allum ......................... 600/595 |
| 6,032,530 A | 3/2000 | Hock |
| 2005/0126026 A1 * | 6/2005 | Townsend et al. ............. 33/512 |
| 2007/0015611 A1 * | 1/2007 | Noble et al. ................. 473/450 |
| 2007/0167671 A1 * | 7/2007 | Miller, III ..................... 600/25 |

* cited by examiner

*Primary Examiner*—Max Hindenburg
*Assistant Examiner*—Brian Szmal
(74) *Attorney, Agent, or Firm*—Stephen M. De Klerk; Sonnenschein, Nath & Rosenthal

(57) ABSTRACT

The present invention relates to a system and method for continually monitoring the spine of a user via device containing electromechanical transducer, processor, delay, transmitter, and a feedback component. Through the device and method of employing, the user will be able to learn and sustain a proper posture, thereby avoiding future back pain.

6 Claims, 5 Drawing Sheets

SPINE TILT MONITOR WITH BIOFEEDBACK

BACKGROUND

Low back pain is a major cause of morbidity, disability, limitation of activity, and economic loss. Most studies have found that 60-80% of people are affected with low back pain at some time during their lives (Hult 1954, Biering-Sorensen 1982, Svensson and Andersson 1982, Frymoyer et al 1983). Some sports have been related to low back and even to sciatica. In particular, sports which involve twisting, such as golf, bowling, and tennis, have been associated with lumbar disc herniations (Iselsey 1975). Other studies have suggested a relationship between mild non-disabling back pain and jogging and cross country skiing. A special example is the relationship between isthmic spondylolisthesis and gymnastics or American football. Regarding spinal posture, in two studies in which the extent of forward flexibility was measured before the occurrence of low back pain (Dieck 1982, Biering-Sorenson 1984), restricted forward flexion was associated with a decreased risk of subsequent low back pain. This result suggests that restricted forward flexion may be indicative of a more stable lumbar spine that is less susceptible to injury (White & Panjabi 1978). It is widely believed in ergonomics that a neutral posture is safer.

Motion sensors for kinetic activities such as golf, tennis and the like have long been known. The use of available feedback to indicate level of accomplishment to the user via pitch, duration or the modulation of either, is frequently used. Feedback with regard to spinal muscle can be considered a case of learning to relax a specific group of muscles with the aid of electronically delivered information. There have been two separate approaches to feedback in the field of back pain: a general relaxation technique and EMG feedback as part of a wider treatment package.

It is an object of the present system to overcome the disadvantages and problems in the prior art. This object is primarily accomplished by monitoring regions of a user's spine during work and physical activities, and providing biofeedback to the user.

DESCRIPTION

The present invention proposes a system and methods for monitoring spinal region of a user and sending biofeedback to the user.

The present invention proposes a method that continually monitors a user's spine in order to prevent or delay the occurrence of pain.

The present invention teaches a system that not only can help to prevent the onset of back pain, but help to train users to maintain back health.

These and other features, aspects, and advantages of the apparatus and methods of the present invention will become better understood from the following description, appended claims, and accompanying drawings where:

FIG. 1(a) exhibits the regions of the spine.

FIG. 1(b) compares improper posture positions that can lead to the onset of back pain with proper positions that can help to prevent back pain.

The following description of certain exemplary embodiment(s) is merely exemplary in nature and is in no way intended to limit the invention, its application, or uses. Throughout this description, the term "biofeedback" refers to a signal, such as electrical, audible, visual, or sensory, that is delivered to a user in response to a previous action taken by the user, in an effort to train the user to control a body function.

Now, to FIGS. 1-4. Whereas FIGS. 1-4 are presented and discussed individually, they, in total, represent the present invention. Unless otherwise noted, the FIGs refer back to and rely upon each other.

Figure 1A:
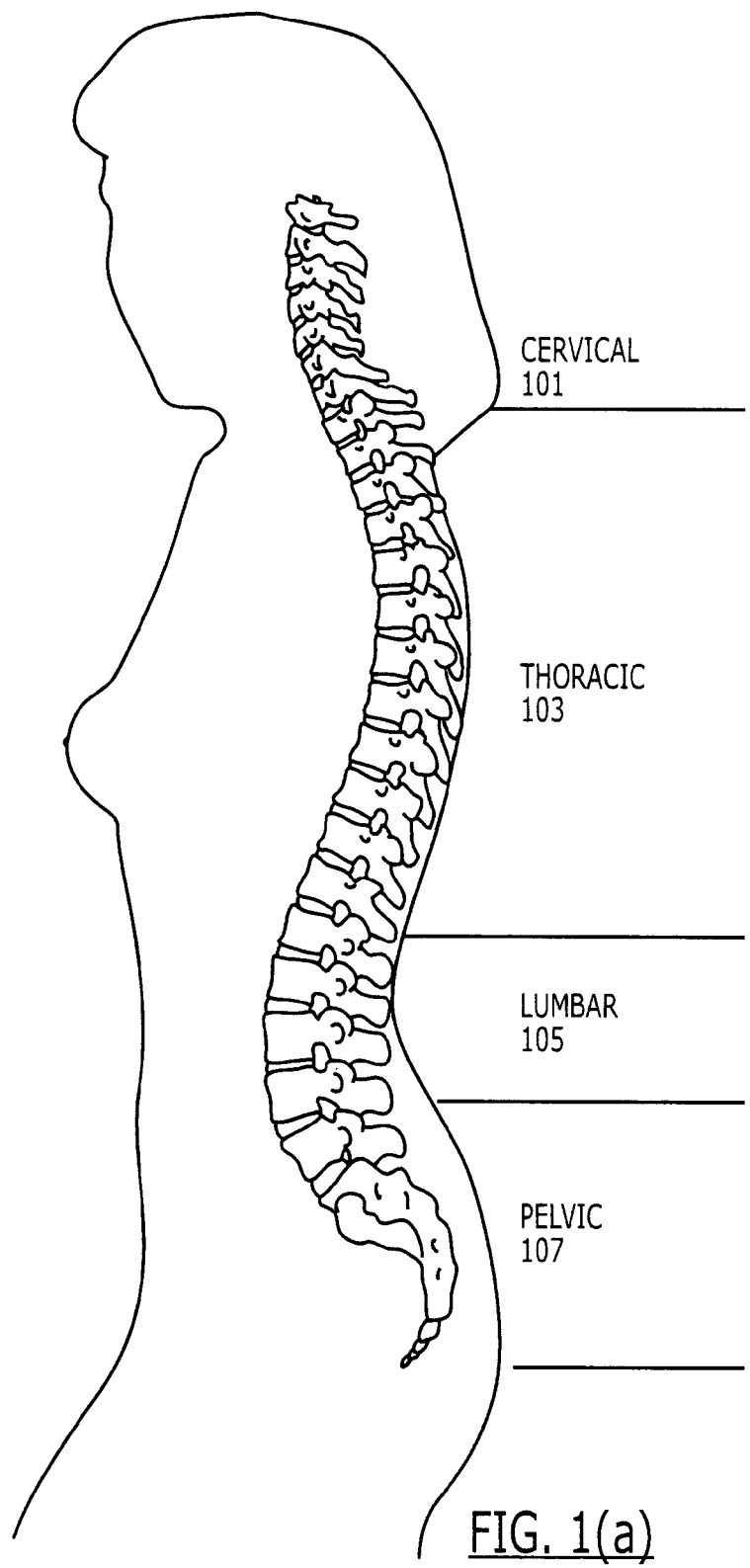

FIG. 1(a) is a graphic of the human spinal column, divided into its various regions, including cervical 101, thoracic 103, lumbar 105, and pelvic 107. Back pain exhibited by the spine, can include neck pain, low back pain, referred pain, and radicular pain. Back pain has been known to be located at or around the cervical region 101 and the lumbar region 105. To the epidemiology of back pain, it has been reported that restricting the forced flexion of posture was associated with a decreased risk of low back pain. This result suggests that restricted forward flexion may be indicative of a more stable lumbar spine that is less susceptible to injury. While not to be bound by theory, it is believed that a posture exhibiting forward flexion will subject the spine to increased compression.

Figure 1B:
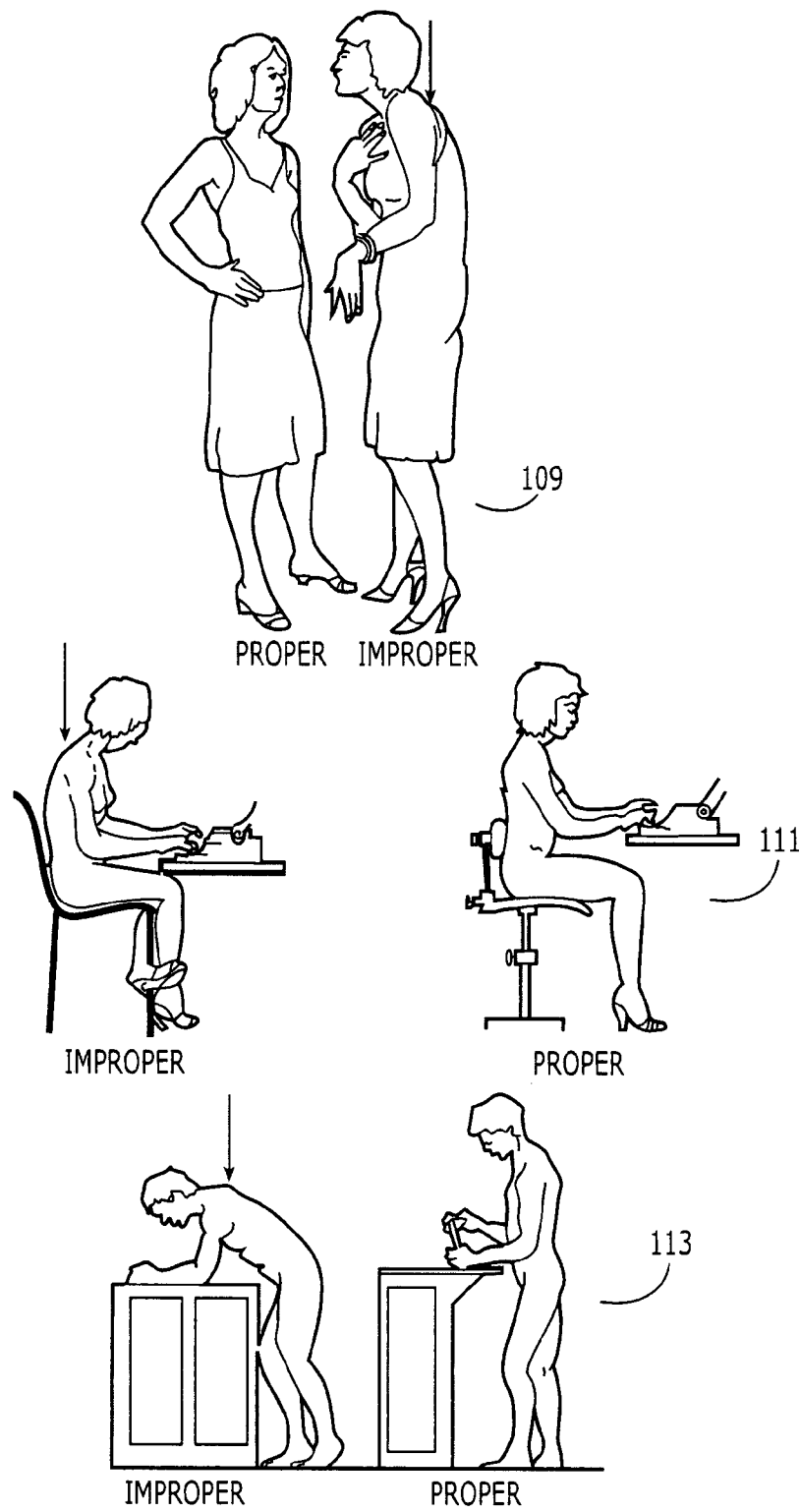

FIG. 1(b) shows posture in forward flexion stance, exhibited in different circumstances: standing 109, working at a desk 111, and working at a standing desk 113. In all circumstances, there is a posture that may be taken which decreases or prevents the occurrence of back pain ("proper"), and a forward flexion posture that may be taken that likely increases occurrence of back pain ("improper"). Through the present invention, it is believed that by maintaining a posture that avoids excessive forward flexion, back pain around the cervical region or lumbar region of the spine can be prevented.

Figure 2:
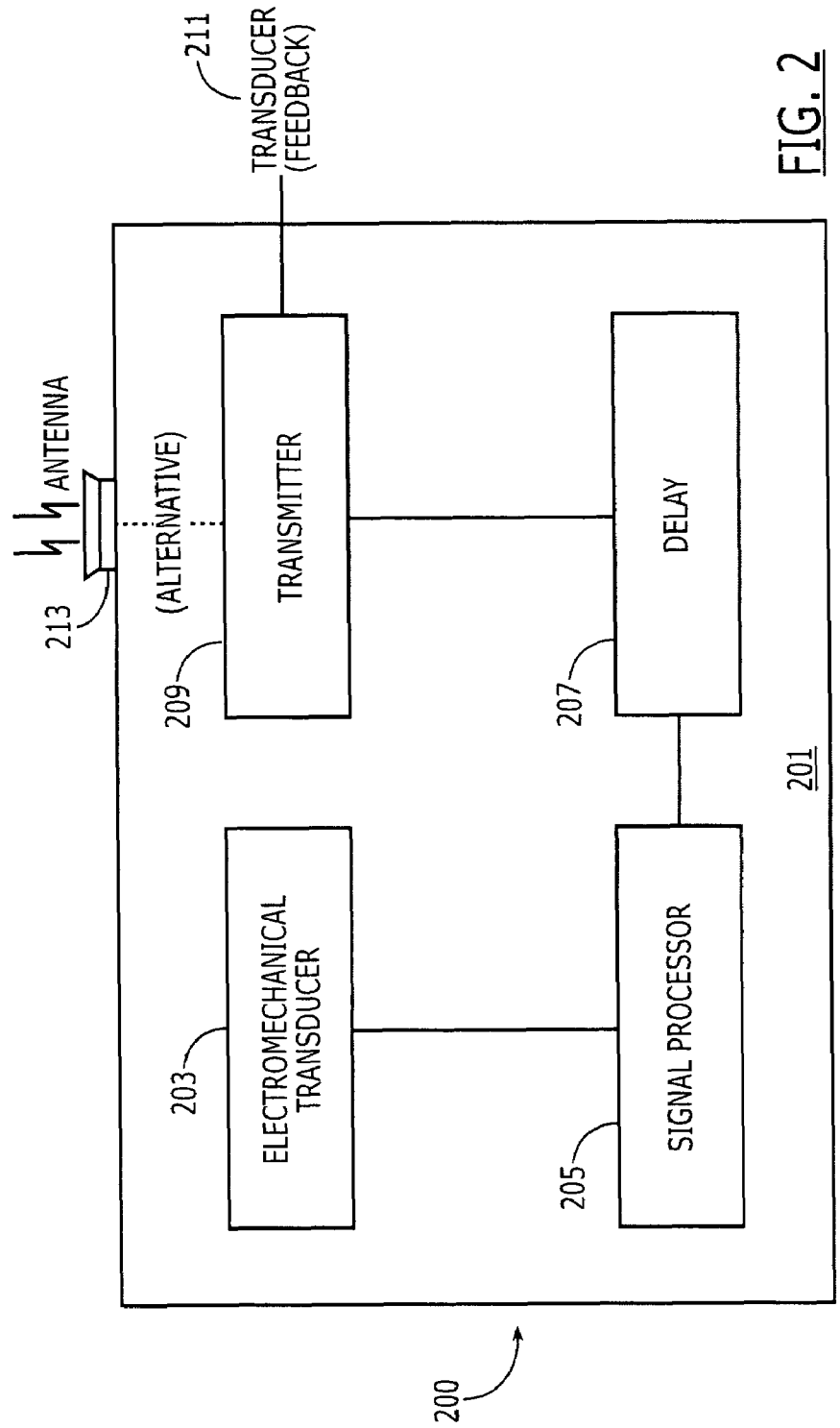
FIG. 2 shows a diagram of the components of a system of the present invention.

FIG. 2 is an embodiment of the spine monitoring device 200 of the present invention, such devices 200 useful for monitoring the position and condition of the spine during work periods and exercise periods. In particular, the device 200 is used to monitor the cervical region and lumbar region of the spine. FIG. 2, while possessing the component parts of the device, is not reflective of the size of the device 200 in reality. In reality, the device 200 measures under 3 cm, preferably less than 2.5 cm. In one embodiment, the device 200 is micro-size, measuring less that several millimeters. The device 200 possesses an electromechanical transducer 203, a signal processor 205, a delay 207, a transmitter 209, and feedback means 211. In an alternatively embodiment, the device 200 possesses an antenna for communication. The various components can be mounted on a base 201, for example a breadboard. In operation, a signal is generated by the device 200 when the electromechanical transducer 203 is affected beyond an optimum set level, such as angle, pressure, or force.

The electromechanical transducer 203 of the device 200 is useful for detecting a change by or being exerted upon the spine, and then communicating a signal to the device 200. Example of transducers include sensors suitable for measuring pressure, force, acceleration, or velocity, such as an accelerometer, barometer, speedometer, and the like. One or more sensors may be used in conjunction. The sensor is used to provide an actual measurement of the position or condition of the spine. This actual measurement is then compared to the optimum setting of position or condition programmed into the device 200. If the actual measurement is over or under (read: + or −) to the optimum setting, the device 200 will indicate such through its feedback means 211. In one embodiment, the actual measurement is provided a % deviation from the optimum setting before a signal is sent through to the feedback means 211. This % deviation can be around +/−5%. In one embodiment, the sensor is angular, i.e., capable of measuring the angle of the cervical region in relation to the spine. In this way, the device 200 is able to monitor the angle of the spine in order to stop forward flexion, and thus prevent back pain.

The signal processor 205 receives the signal from electro-mechanical transducer 203 for modification into an acceptable form for the rest of the system 200. The processor 205 can include a micro processor, a rectifier, a transistor, comparator circuitry, digital component for example AND, OR, NOR, and the like, wave modulator, wave generation, amplifier, one or more in conjunction or used individually. In one embodiment, memory storage means may be connected to the processor 205, for example RAM or ROM (not shown). User interfaces that are used to program, set, and operate the device may interact with the various components via the processor 205, for example buttons, knobs, switches, keyboard, etc.

The delay 207 is essentially a gate component, suitable for determining when the signal from the processor has met the requirement that allows it to be forwarded to the feedback means 211. The delay 207 can be based on time, current flow, or energy capacitance. In one embodiment, upon the signal flowing from the processor 205, and delivered to the delay 207, a timer is initited. The timer can be countdown or count up. If the signal continues to flow for a sufficient period of time, the delay gate will allow the signal to flow through. In one embodiment, the period of time may be 1 second to several seconds, for example 3 to 5 seconds. In another embodiment, the delay gate may be an energy storage component, wherein when the capacitance of the delay, for example a capacitor or inductor, has been reacted, the signal is passed through. In an embodiment, the capacitance can range from about 0.001 µF to about 0.1 µF.

The transmitter 209 of the device 200 can be used to deliver the signal directly to the feedback means 211, amplify the signal prior to delivery to the feedback means 211, and/or split the signal for a variety of delivery avenues. In one embodiment, the transmitter can be a switch that is actuated upon the delivering of the signal from the delay 207. The transmitter 209 can also include encoding or signal conversion technology, allowing the signal to be converted into other forms such as light. In one embodiment, the signal via the transmitter is provided to a feedback means 211 and a communication means such as an antenna 213. In this way, the feedback means 211 can communicate to the user the position or condition of the spine, and the signal can also be communicated to another source, such as a computer, recording equipment, and the like. In another embodiment, the communication means is wired, such as a fiber optic line. For wireless communication means, WIFI or RF technology (Bluetooth™) may be employed. The communication to another source can allow the collection of cervical and/or lumbar kinetic or kinematic data under a variety of exercise regimes, work regimes, and activities of daily living.

The base 201, as previously stated, may be a breadboard. The base 201 may also resemble a design suitable to allow it be body-mountable on the user, for example an inner ear piece, a head set, or a set to allow it to be strapped to the body with a belt. The base 201 can also be in two or more pieces, allowing sections of the device 200 to be carried on different parts of the body, for example the feedback means 211 can be stored within an ear piece, while the transducer 201, processor 205, delay 207, transmitter 209, and antenna 213 can be stored within a set box carried on the waist.

The feedback means 211 is used to provide an indicator to the user when the spine position or condition changes beyond the optimum setting outside the allowable deviation. The feedback means 211 can be an audible device, sensory device, visual device, and the like. Audible devices can include alarms, buzzers, etc. In one embodiment, the audible device can be fitted to the ear. Sensory devices can include electro-stimulators capable of providing a mild but effective shock to the body of the user or a localized vibration. Such sensory devices can be applied to any body part, for example a finger. Visual devices can include monitors, such as TV monitors, allowing the users to see the movement of various regions of the spine.

Figure 3:
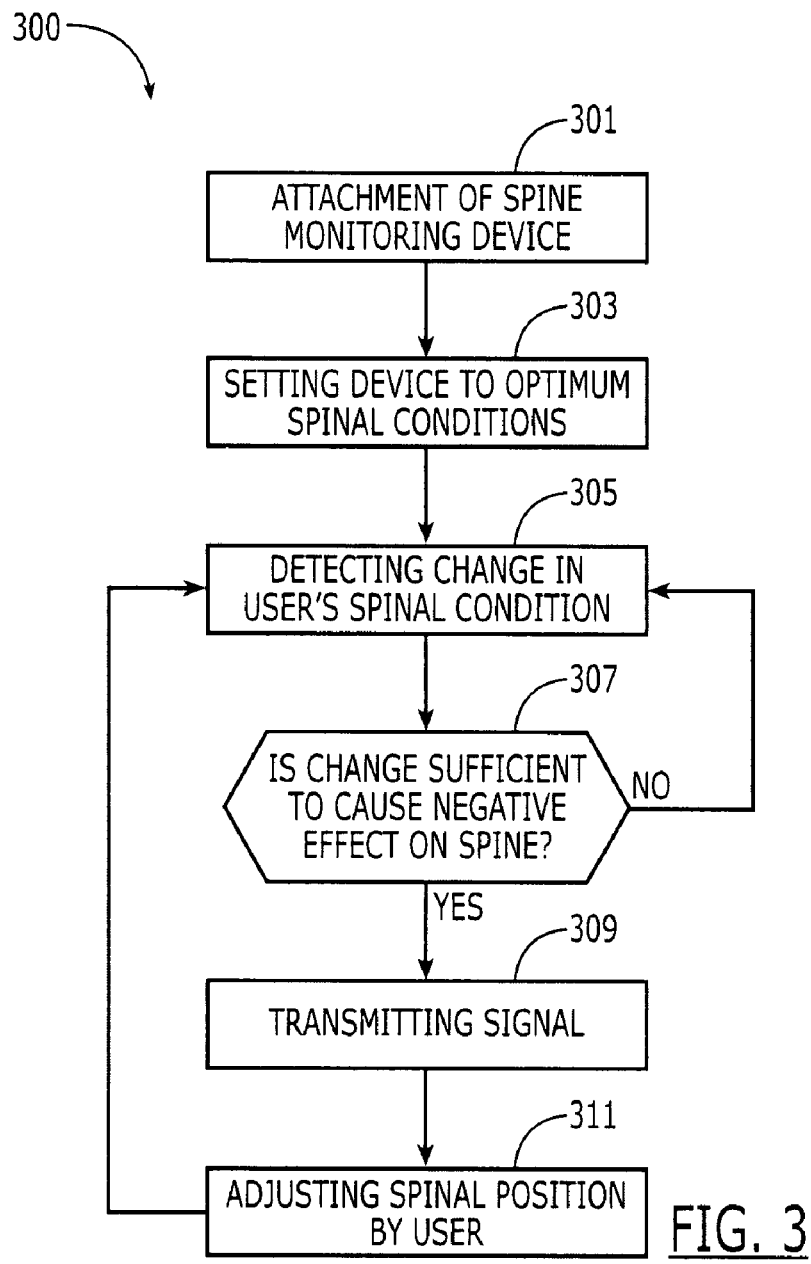
FIG. 3 shows a method of monitoring the spine condition and position according to the present invention.

FIG. 3 is an embodiment of a method of monitoring the spine 300 of the present invention, comprising the steps of attaching a spine monitoring device 301, setting the optimal spine position and/or conditions on the device 303, detecting a change in the user's spinal condition or position 305, determining if the change is sufficient 307, and if so, transmitting a signal through the device 309, and adjusting the position of the user's spine 311. The method contains a loop function, allowing continual detection of the user's spine condition while the device is in use.

Attaching the monitoring device 301 to the user can include attaching the devices as a complete unit to a body part of the user, such as, for example, fitting it an ear. The device can also be attached adjacent to the spine, such as on a bony landmark, e.g. L3, with a strapping means such as a belt. If the device is comprised of components separately connected, they can be attached to the body in different locations. Preferably, the device is attached in a location such that it does not interfere with normal movement of the user. In this way, accurate monitoring of the spine's condition and/or position can be made.

Setting the optimal spinal conditions on the device 303 is performed to input into the device the most suitable condition and/or position of the user's spine for the avoidance of present or future back pain. The condition and/or position includes spine angle, pressure placed upon the spine, force upon the spine, acceleration by which the spine changes its angle, or velocity by which the spine changes. The most suitable condition and/or position refers to the measurements that are most likely to avoid or prevent the occurrence of back pain. The most suitable condition is preferably specific for each person, and can be determined by previous tests' on the user's spine. The setting on the device is reflective of the most suitable condition and/or position with an allowable deviation. The deviation may be around +/−5%. The device may be set by user interfaces including switches, dials, buttons, or computer devices whereby the device is connected to the computer, such computer including software allowing control or setting of the devices.

The device is then prepared to detect change in the condition and/or position of the user's spine 305. Change includes a change in the pressure, force, acceleration, angle, or velocity exhibited by the user's spine. The device, continually monitoring, will detect the change when a measurement including the deviation is made. Upon the detection of a change, a signal will be sent through the device.

A determination will then be made as to whether the signal is sufficient to cause a present or future negative effect on the spine 307. The signal will be determined sufficient based on time or signal level, for example, after the signal occurs for a certain period of time, it is determined sufficient. The period of time can be from 30 second to 1 minute. A negative effect on the spine includes neck pain, back pain, spinal disk injury, spinal inflammation, and sciatica. The negative effect can be to enhance a current status or to initiate a spinal injury. If the change is not sufficient, the signal is looped back toward detection for continual monitoring. If the change is sufficient, the signal is then transmitted.

Transmitting the signal 309 can include directing the signal in one or more directions. The directions include a biofeedback means and a communication means. As stated previously, the biofeedback means includes audible devices, sensory devices, and visual devices. Communication means can include wireless technology such as an antenna, and wired technology such as fiber optic. By the signal being directed to the biofeedback means, the user is able to adjust his/her spine condition and/or position to bring it again with the optional settings.

Adjusting the spinal position 311 can include adjusting the posture, adjusting the shoulders, adjusting the head, modifying the movement of the body, swing of the arms, and the like. As the adjustment will be temporary and the user will likely go back to his/her original poor posture position, the signal will be looped, allowing for continual monitoring of the spine. Thus, the user will be continually trained, eventually leading to a preferred spinal condition and/or position that will be least likely to cause a present or future negative effect to the spine.

Figure 4:
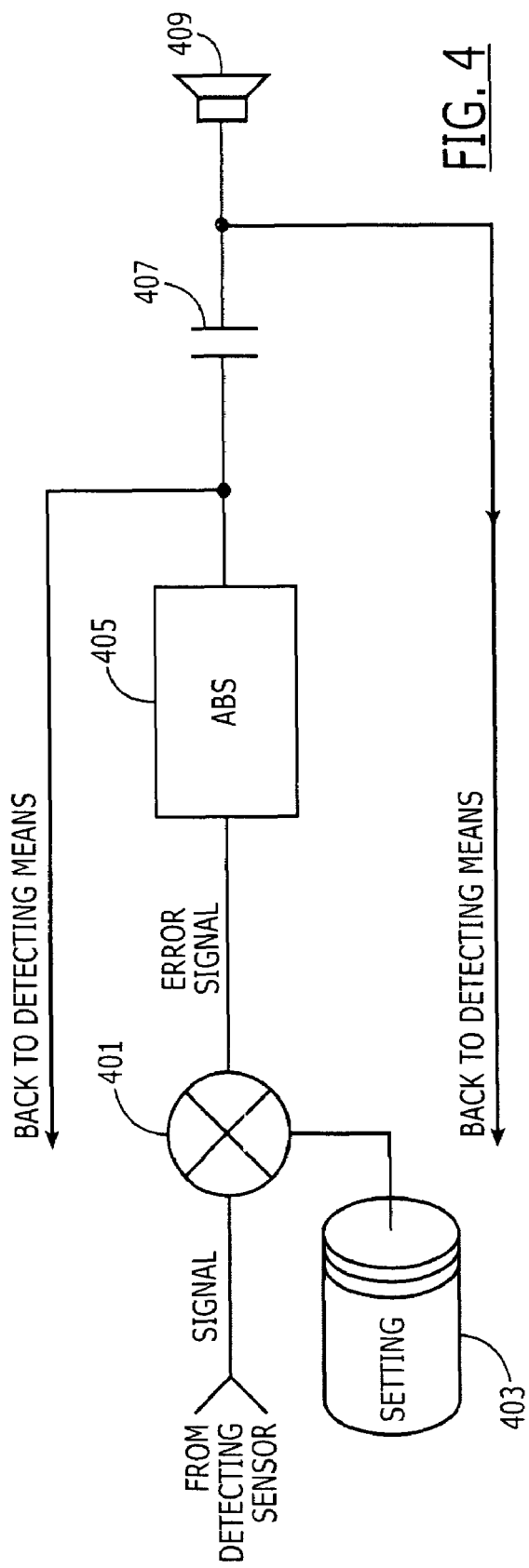
FIG. 4 is a schematic example of a system for determining whether a spine condition or position, and components for providing biofeedback.

FIG. 4 is an example of a schematic of the present invention, wherein the signal is determined as sufficient to cause a negative effect on the spine, and then forwarded through the biofeedback means. The schematic exhibits a comparator circuit, a storage 403, an absolute value generator 405, a capacitor 407, and an audible device 409.

As shown in the schematic, as the signal comes from the detecting sensor, it can be inserted into a comparator 401 for comparison against the optimum settings. The comparator circuit 401 can be a subtractor. The optimum setting, as entered into the device via user interfaces, can be stored on a register 403, such as a RAM or ROM. The comparison of the actual signal and the optimum setting will produce an error signal. The error signal can be passed through an absolute value generator 405 to ensure a positive value. The signal will then be forwarded to a energy storage device 407, such as a capacitor. If the signal is sufficient to cross the storage device, the signal will be passed through to the audible device 409. If the signal is not sufficient, it will simply be delivered back to the detecting sensor for continual monitoring. Audible devices 409 include speakers and earphone devices. Even if the signal is delivered to the audible device 409, a signal is sent to allow for continual monitoring.

Having described embodiments of the present system with reference to the accompanying drawings, it is to be understood that the present system is not limited to the precise embodiments, and that various changes and modifications may be effected therein by one having ordinary skill in the art without departing from the scope or spirit as defined in the appended claims.

In interpreting the appended claims, it should be understood that:

a) the word "comprising" does not exclude the presence of other elements or acts than those listed in the given claim;

b) the word "a" or "an" preceding an element does not exclude the presence of a plurality of such elements;

c) any reference signs in the claims do not limit their scope;

d) any of the disclosed devices or portions thereof may be combined together or separated into further portions unless specifically stated otherwise; and e) no specific sequence of acts or steps is intended to be required unless specifically indicated.

The invention claimed is:

1. A method for preventing back pain, comprising the steps of:
   attaching a spine monitoring device to a user;
   setting said device by inputting a most suitable spinal condition or position during work periods;
   detecting a change in the spine to said user, wherein said change is forward flexion;
   determining whether said change is sufficient to cause a negative effect on spine;
   If change is sufficient, then steps a)-b),
      a) transmitting a signal to said user; and
      b) adjusting the spine of said user;
   and
   continuing to monitor said user's spine,
wherein said change is sufficient when said change is more than around +/−5% of said most suitable condition.

2. The method for preventing back pain of claim 1, wherein attaching said spine monitoring device occurs at said user's ear.

3. The method of preventing back pain of claim 1, wherein said condition or position includes spine angle, pressure placed upon the spine, force on the spine, acceleration by which the spine changes said angle, or velocity by which the spine changes.

4. The method of preventing back pain of claim 1, wherein setting said device occurs via user interfaces.

5. The method of preventing back pain of claim 1, wherein transmitting said signal comprises transmitting an audible signal, visual signal, or sensory signal.

6. The method of preventing back pain of claim 1, wherein said negative effect can be selected from the group consisting of neck pain, back pain, spinal disk injury, spinal inflammation, and sciatica.

* * * * *